United States Patent [19]

Eguchi

[11] Patent Number: 4,465,070
[45] Date of Patent: Aug. 14, 1984

[54] STITCHING FORMATION BY A SUTURING INSTRUMENT

[75] Inventor: Yasukata Eguchi, Tokyo, Japan

[73] Assignee: Janome Sewing Machine Co., Ltd., Tokyo, Japan

[21] Appl. No.: 348,457

[22] Filed: Feb. 12, 1982

[30] Foreign Application Priority Data

Apr. 14, 1981 [JP] Japan ................................. 56-54975

[51] Int. Cl.³ ...................... A61B 17/04; D05B 97/00
[52] U.S. Cl. ................................ 128/334 R; 128/340; 112/169
[58] Field of Search .................. 128/334 R, 335, 340; 112/169

[56] References Cited

U.S. PATENT DOCUMENTS

| | | | | |
|---|---|---|---|---|
| 2,327,353 | 8/1943 | Karle | ................................... | 128/340 |
| 2,580,964 | 1/1952 | Skaller | ................................ | 112/169 |
| 3,957,004 | 5/1976 | Ketterer et al. | ..................... | 112/169 |
| 4,123,982 | 11/1978 | Bess et al. | ............................ | 112/169 |

Primary Examiner—Dalton L. Truluck
Attorney, Agent, or Firm—Michael J. Striker

[57] ABSTRACT

A suturing instrument is used to form stitchings including stitching formation made by causing a shuttle thread to move in reciprocation on cut edges of a human part, between knottings and next knottings in a lock stitching, via an outer side of a needle thread at a needle-out-hole from a needle-in-hole of a needle, thereby to make conglutination of the cut part stable and sound. In a method of suturing cut edges of human parts in a surgical operation the shuttle thread crossed with the needle thread traverses over the cut edges from the needle-out-hole to the needle-in-hole of the next stitch and passes under the outside of the needle thread carried by the needle. The shuttle thread then again traverses over the cut edges to the needle-out-hole of the next stitch.

2 Claims, 13 Drawing Figures

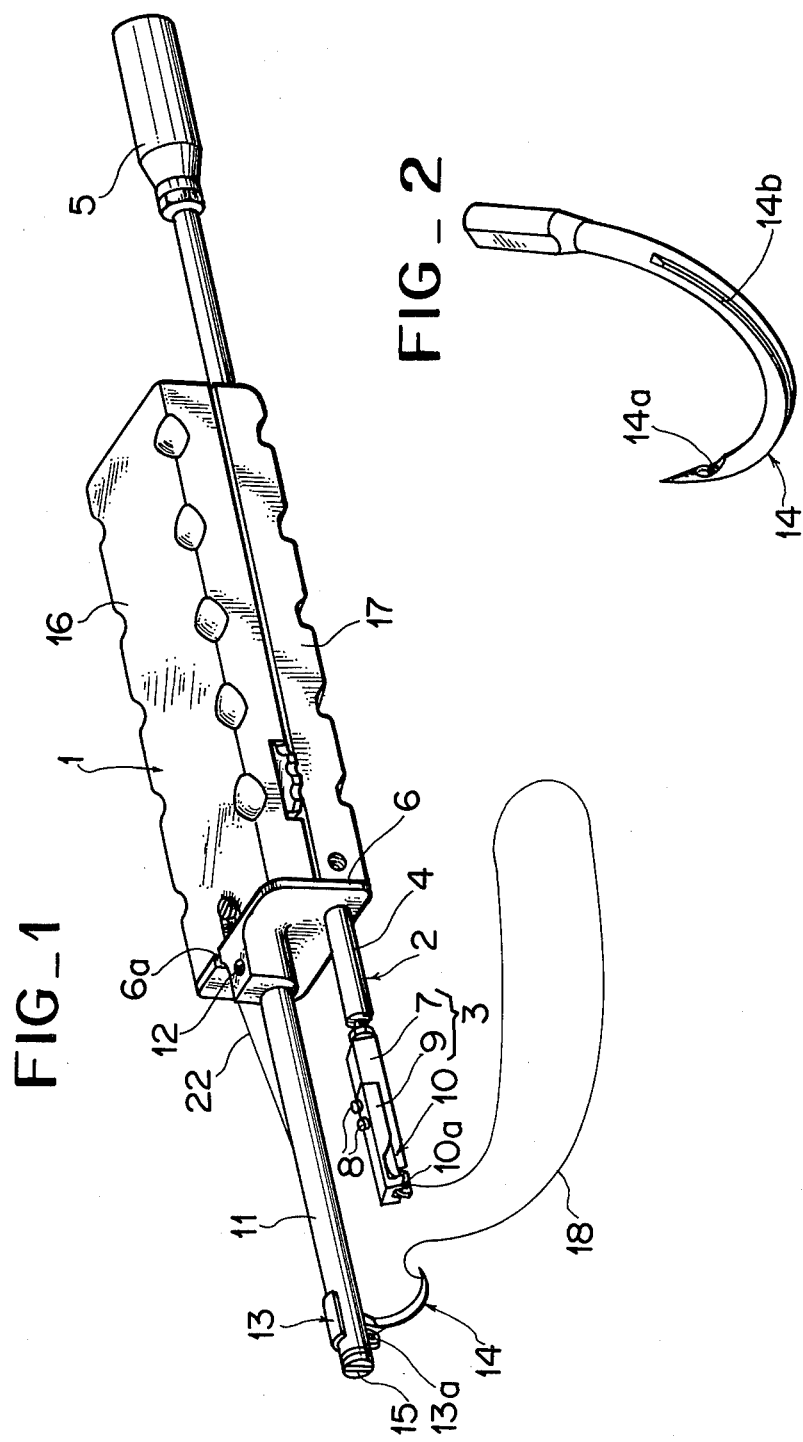

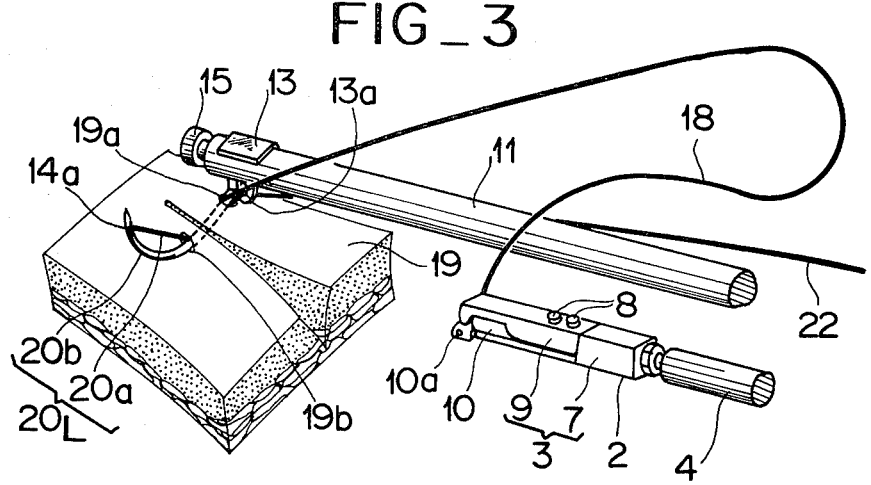
FIG_3
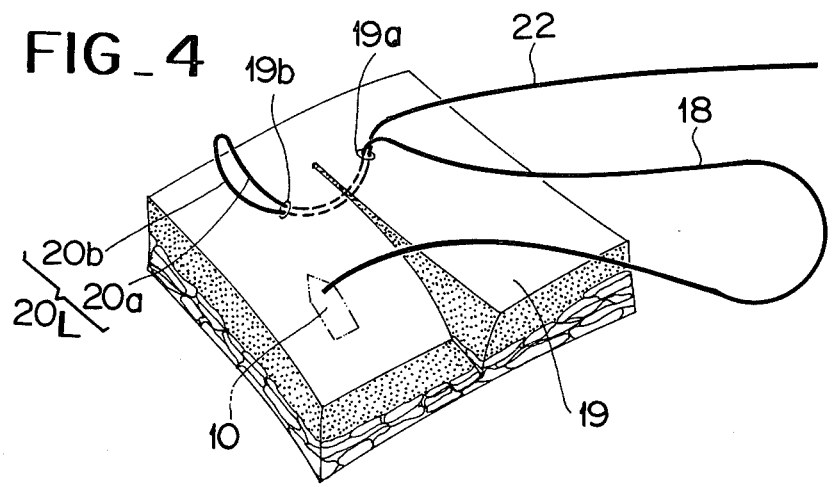
FIG_4
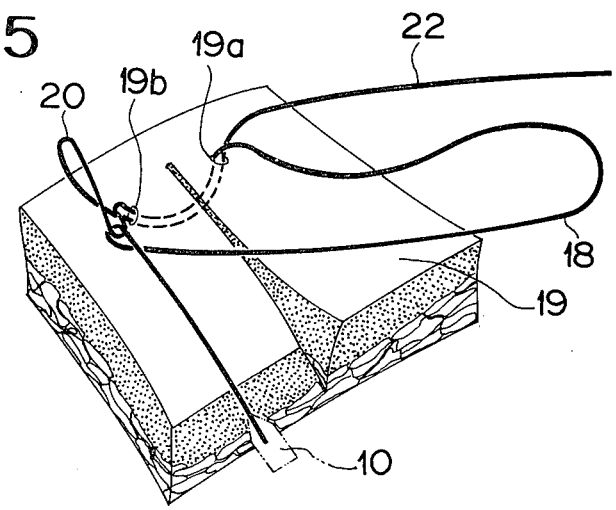
FIG_5

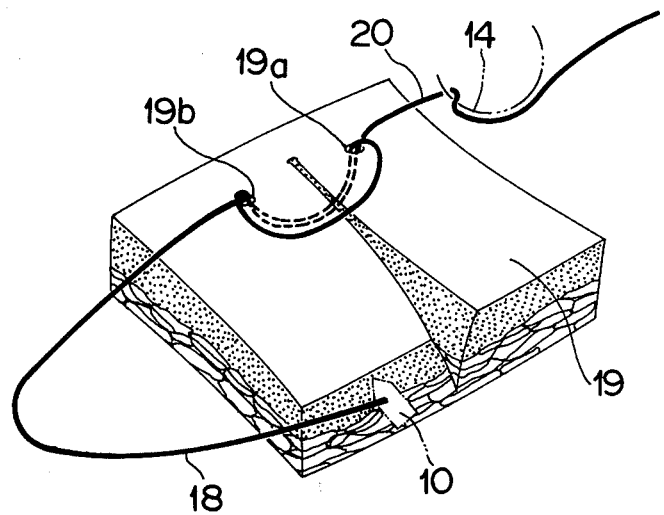
FIG_6
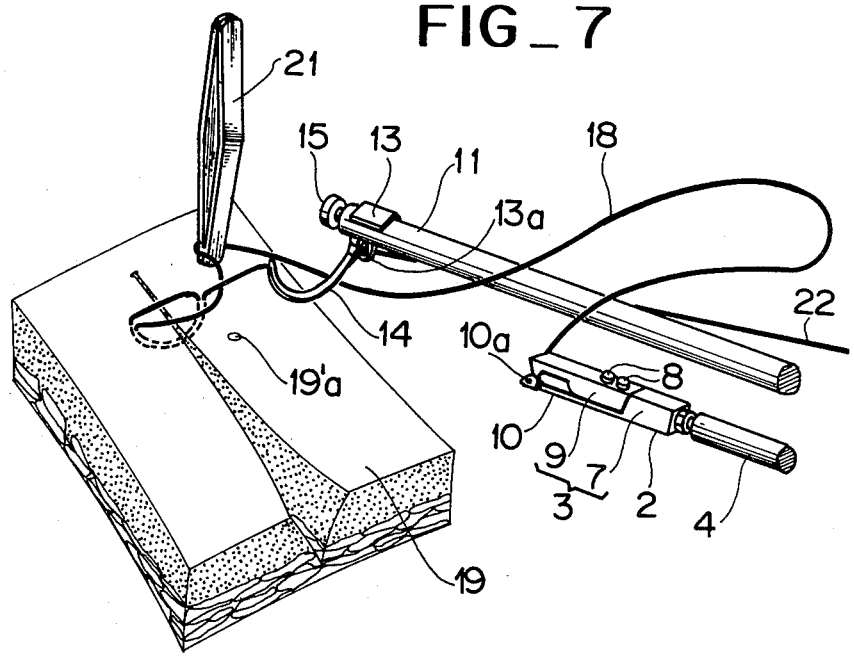
FIG_7

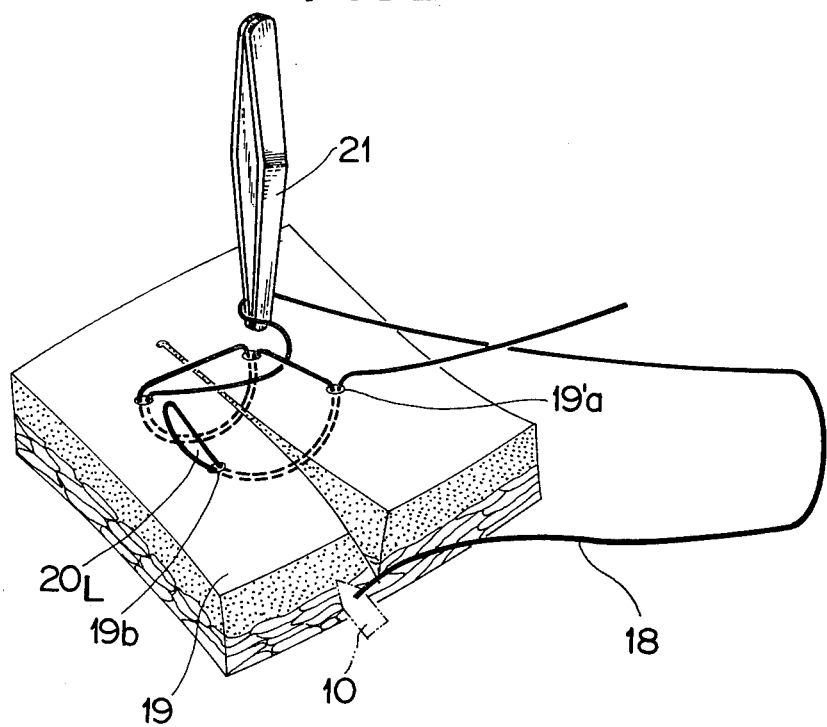
FIG_8
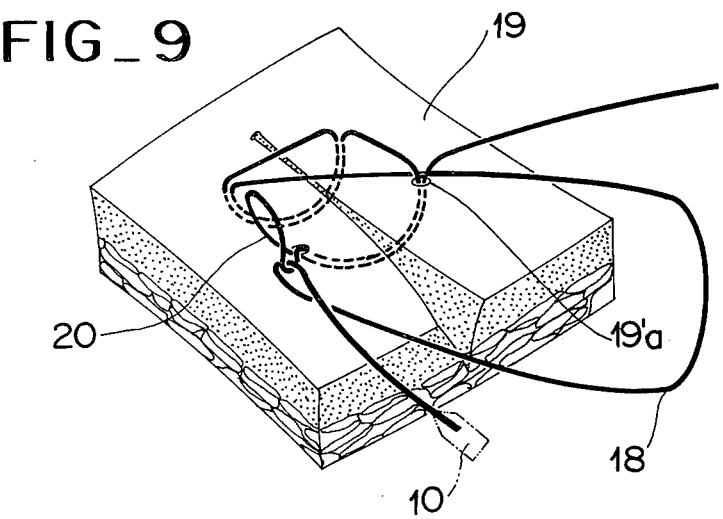
FIG_9

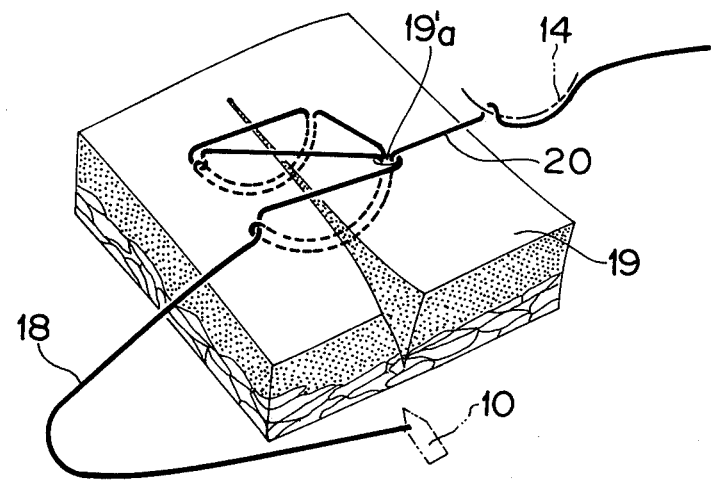
FIG_10
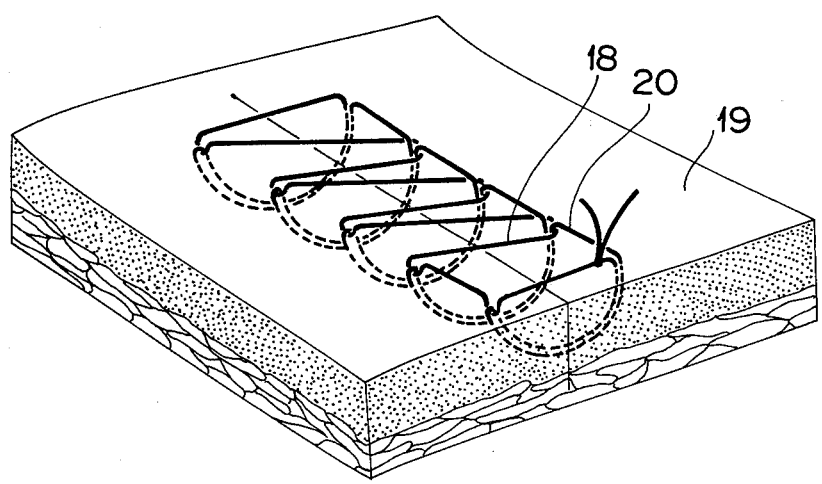
FIG_11

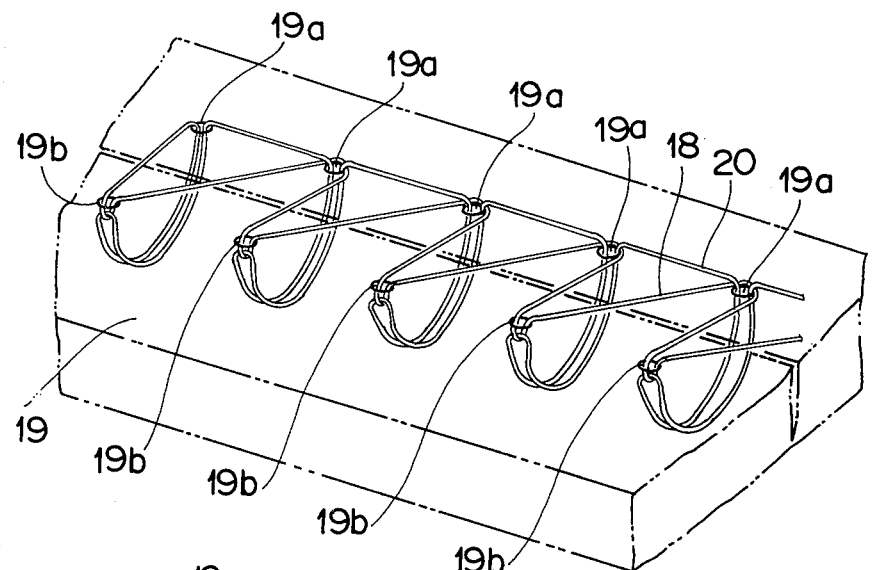
FIG_12
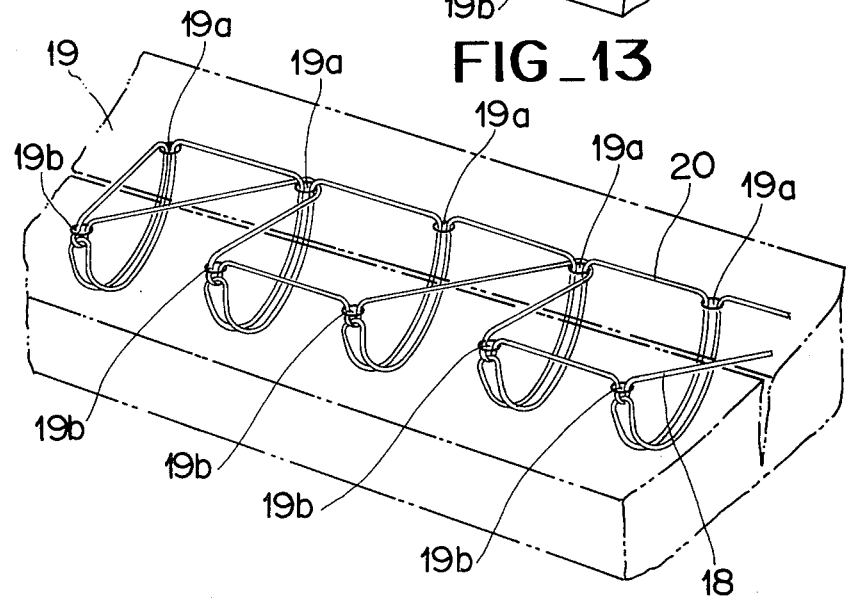
FIG_13

STITCHING FORMATION BY A SUTURING INSTRUMENT

BACKGROUND OF THE INVENTION

The invention relates to a suturing stitch formation by means of a suturing instrument which carries out suturing in a lock stitching practice on a human part to be sutured with a suturing thread connected to a shuttle and a suturing thread connected to a needle.

SUMMARY OF THE INVENTION

An object of the invention is a method for surgical suturing by means of a suturing instrument so as to form stitchings including stitching formation made by causing a shuttle thread to move in reciprocation on cut edges of the human part, between previous knottings and next knottings in the lock stitchings, via an outer side of a needle thread, a needle-out-hole and a needle-in-hole of the needle, thereby to make conglutination of the cut part stable and sound.

BRIEF DESCRIPTION OF THE DRAWINGS

FIG. 1 is a perspective view of a suturing instrument;

FIG. 2 is a perspective view of a curved needle;

FIG. 3 is a perspective view showing a suturing condition with the suturing instrument for a surgical operation;

FIGS. 4 to 6 are perspective views showing the suturing processes after an initial penetration of a curved needle in relation between the needle thread of which and the shuttle thread, FIG. 4 is a view showing relation between the needle thread and the shuttle thread in the condition of FIG. 3, FIG. 5 is a view showing a condition of locking the shuttle thread and into a loop of the needle thread, FIG. 6 is a view showing a condition of tightening the needle thread and the shuttle thread;

FIG. 7 is a view showing relation between the needle thread and the shuttle thread at a second penetration of the curved needle;

FIG. 8 is a view showing a condition of forming a loop of the needle thread;

FIG. 9 is a view showing a condition of locking the shuttle thread into the loop of the needle thread;

FIG. 10 is a view showing a condition of tightening the needle thread and the shuttle thread;

FIG. 11 is a view showing a condition of completing the suturing;

FIG. 12 is a detailed view of stitchings of FIG. 11; and

FIG. 13 is a detailed view of stitchings formed by a different operation from the operation forming the stitchings shown in FIG. 12.

DETAILED DESCRIPTION OF THE PREFERRED EMBODIMENTS

The present invention will be explained with reference to an embodiment according to the invention. The numeral 1 represents the suturing instrument of the invention for the surgical operation to be used for forming stitchings. The numeral 2 is a shuttle holding member composed of a shuttle holding portion 3, a rod 4 and an operating handle 5. The shuttle holding member 2 is slidably reciprocated in an axial direction within determined range under condition that the rod 4 is restrained in rotation with respect to a main body 6 of the suturing instrument 1, and the shuttle holding portion 3 is effected with the same movement by pushing operation of the handle 5.

The shuttle holding portion 3 is composed of a shuttle holder 7 and a shuttle hook 9 secured to the shuttle holder 7 by a screw 8. Between the holder 7 and the hook 9, a shuttle 10 is held, so that a loop of a needle thread runs as later will be mentioned between the shuttle hook 9 and an upper surface of the shuttle, and it returns between the shuttle holder 7 and a lower surface of the shuttle.

A needle bar 11 is fixed at its one end to the main body 6 by a screw 12 and is provided on the other end with a guide piece 13 for detachably holding a curved needle 14 by a screw 15.

The curved needle 14 is, as shown in FIG. 2, formed with a needle eye 14a and defined with an oblong groove 14b for guiding the thread halfway of an outer circumference thereof up to the needle eye 14a.

The main body 6 of the suturing instrument 1 is detachably attached with a thread supply (not shown) thereon for coiling a suturing thread 22. The thread from the thread supply is effected with tension by a thread tension mechanism provided on the main body 6, and is drawn out from a thread guiding groove 6a of the main body 6. The main body 6 is detachably covered with a cover 16.

A reference will be made to an order of stitching formation by means of the suturing instrument 1 for the surgical operation. The sequence in operation comprises, prior to the suturing, taking off a cover 16 from the suturing instrument 1, furnishing the thread supply coiling with the suturing thread 22 within the main body 6, giving tension to the suturing thread 22 by the thread tension mechanism and inserting the thread into a guide hole 13a of the thread guide piece 13 via the thread guide groove 6a, passing the thread 22 through the needle eye 14a along the oblong groove 14b of the curved needle 14, drawing the thread 22 as much as for a suturing length, and combining its end to a thread hole 10a of the shuttle 10 supported between the shuttle holder 7 and the shuttle hook 9 to make a suturing thread 18 at the shuttle side (called as "shuttle thread" hereafter). The shuttle 10 is drawn toward the main body 6 together with the shuttle thread 18 before penetration of the curved needle into a human part 19 to be sutured in order to avoid hindering the penetration of the curved needle.

When the curved needle 14 is penetrated into the part 19 from a needle penetrating hole 19a, a part 20a of the needle thread pulled in straight (as shown in FIG. 3) between the needle eye 14a and a needle getting-out-hole 19b, is changed into a loop 20L of crescent of the needle thread together with a part 20b of the needle thread guided in an oblong groove 14b. The shuttle 10 connected with the shuttle thread 18 is moved to a remote side from the main body 6 and is advanced into a needle thread loop 20L to catch this loop, and then if the shuttle 10 is returned to the main body 6, the shuttle 10 makes a round about the thread part 20b. That is, when the shuttle 10 is moved to the remote side from the main body 6, the needle thread part 20a runs between the shuttle hook 9 and the upper surface of the shuttle 10, and reaches at the back side of the shuttle 10, and when the shuttle 10 is returned to the main body 6, the needle thread part 20a runs between the shuttle holder 7 and a lower surface of the shuttle 10, so that the shuttle thread 18 and the needle thread are crossed as shown in FIG. 5. Subsequently, the curved needle 14 is pulled out from the needle-in-hole 19a and the needle thread 20 and the shuttle thread 18 are tightened to form an initial stitch of lock stitch. Under condition that the shuttle thread 18 is moved apart from cut edges of the part 19 by a pincette 21 shown in FIG. 7, the curved needle 14 is penetrated into a next penetrating portion 19'a, and a loop 20L of the needle thread is formed as shown in FIG. 8. The shuttle 10 is reciprocated to lock the needle thread 20 and the shuttle thread 18 as shown in FIG. 9, and the curved needle 14 is pulled out from the penetrating hole 19'a (represented with "19a" hereafter). Then the needle thread 20 and the shuttle thread 18 are tightened, whereby the stitchings are formed by moving in reciprocation the shuttle thread 18 over the cut edges, and finally the needle thread 20 and the shuttle thread 18 are locked to form stitchings as shown in FIG. 11.

With respect to the stitchings according to the above mentioned suturing operation, the shuttle thread crossing with the needle thread 20 in the lock stitch traverses from the needle-out-hole 19b to the needle-in-hole 19a over the cut edges, as shown in FIGS. 11 and 12, and passes as going round the outside of the needle thread 20 nearly the needle-in-hole 19a, and again traverses over the cut edges to the needle-out-hole 19b, whereby the conglutination is made sound.

In the above mentioned example of the stitchings, since the curved needle 14 is penetrated with respect to the cut edges, one side of the shuttle thread 18 traverses in obliquity and the other side thereof traverses in right angle with respect to the cut edges. Said one side and the other side are different in length, but if considering the penetrating angle of the curved needle 14, the shuttle thread 18 runs in zigzag over the cut edges with the same length of the both sides.

In the above mentioned suturing operation, the shuttle thread 18 is moved by the pincette 21 per each of penetrations, to the remote side from the cut edges for a next penetrating position 19'a, but if said operation is participated on half way of the suturing, the shuttle thread locking with the needle thread 20 in the lock stitching traverses over the cut edges from the needle-out-hole 19b to the penetration hole 19a, and passes as going round the outside of the needle thread 20 nearly the needle-in-hole 19a, and again traverses over the cut edges to the needle-in-hole 19b, thereby to form the stitchings including the stitch formation locking the needle thread 20. Also by this stitching, the cut edges may be adhered.

I claim:

1. A method of suturing cut edges of human parts in a surgical operation by means of a suturing instrument having a curved needle with a needle eye carrying a needle thread and a shuttle carrying a shuttle thread and adapted to reciprocate towards and from the curved needle, wherein lock stitches are formed by penetrating the curved needle into human parts through needle penetrating holes and needle-getting-out holes arranged in pairs at opposite sides of the cut edges and crossing the needle thread and the shuttle thread at said needle-getting-out holes by reciprocating movement of the shuttle and pulling the needle out from said needle penetrating holes, the method comprising the steps of crossing said needle thread with said shuttle thread at a one needle-getting-out hole of one pair of said holes, continously traversing the cut edges of human parts in an oblique direction to the cut edges of human parts with said shuttle thread from said one needle-getting-out hole to a needle penetrating hole of the next pair of said holes displaced a distance from said one pair of holes wherein the needle penetrating holes of said one pair and said next pair of holes are disposed on the same side of the cut edges of human parts, passing said shuttle thread outside and around said needle thread at the needle penetrating hole of said nest pair of holes and traversing the cut edges of human parts at a right angle to the cut edges of human parts with said shuttle thread from said needle penetrating hole of said next pair of holes to a needle getting-out hole of said next pair of holes displaced a distance from said needle getting out hole of said one pair of holes to form a lock stitch wherein said both needle getting out holes of said one pair and said next pair of holes are disposed on the same side of the cut edges of human parts and opposite to the side of the cut edges of human parts containing said both needle penetrating holes of said one pair and next pair of holes.

2. The method of claim 1, wherein an initial lock stitch is formed by passing a needle thread through the needle's eye, connecting the end of the needle thread to the shuttle to form the shuttle thread, penetrating the human parts with the curved needle through the needle penetrating hole and the needle-getting-out hole of said one pair of holes and forming a needle thread loop, advancing the shuttle to the needle to catch said loop, crossing the needle thread and the shuttle thread at the needle-getting-out hole of said one pair of holes by reciprocating the shuttle, and pulling the needle out from the human parts whereby the needle thread and the shuttle thread are tightened.

* * * * *